United States Patent
Yamashita

(10) Patent No.: US 9,398,888 B2
(45) Date of Patent: Jul. 26, 2016

(54) RADIATION IMAGING SYSTEM AND METHOD FOR CONTROLLING THE SAME

(71) Applicant: CANON KABUSHIKI KAISHA, Tokyo (JP)

(72) Inventor: Hironori Yamashita, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 112 days.

(21) Appl. No.: 14/305,525

(22) Filed: Jun. 16, 2014

(65) Prior Publication Data

US 2014/0369466 A1 Dec. 18, 2014

(30) Foreign Application Priority Data

Jun. 18, 2013 (JP) ................................. 2013-127974

(51) Int. Cl.
*A61B 6/00* (2006.01)

(52) U.S. Cl.
CPC ................. *A61B 6/487* (2013.01); *A61B 6/465* (2013.01); *A61B 6/467* (2013.01); *A61B 6/481* (2013.01); *A61B 6/485* (2013.01); *A61B 6/486* (2013.01); *A61B 6/504* (2013.01); *A61B 6/5235* (2013.01)

(58) Field of Classification Search
CPC ........ A61B 6/465; A61B 6/467; A61B 6/481; A61B 6/487; A61B 6/504; A61B 6/507
See application file for complete search history.

(56) References Cited

U.S. PATENT DOCUMENTS

| 4,533,946 | A | 8/1985 | Yasuhara et al. |
| 7,536,633 | B2 | 5/2009 | Faraday et al. |
| 2004/0032412 | A1 | 2/2004 | Odom |
| 2005/0097471 | A1 | 5/2005 | Faraday et al. |
| 2009/0257554 | A1* | 10/2009 | Parks ........................ A61B 6/12 378/44 |
| 2013/0231758 | A1 | 9/2013 | Kim et al. |
| 2013/0343511 | A1* | 12/2013 | Shukla ................... A61B 6/032 378/6 |

FOREIGN PATENT DOCUMENTS

JP 06-154196 A 6/1994

* cited by examiner

*Primary Examiner* — Glen Kao
(74) *Attorney, Agent, or Firm* — Canon USA Inc., IP Division

(57) ABSTRACT

In a radiation imaging system performing a difference process using a stored mask image based on a radiation image obtained before a contrast agent is injected and a radiation image obtained after the contrast agent is injected, a controller displays a first graphic representing a first timing when irradiation of a radial ray is started, a second graphic representing a second timing when the mask image is stored, and a third graphic representing a third timing when the contrast agent is injected in this order along a time axis and controls the second and third timings by the second and third graphics. The controller moves, when one of the second and third graphics is moved along the time axis, the other of the second and third graphics such that an interval between the first and third graphics becomes larger than an interval between the first and second graphics.

10 Claims, 9 Drawing Sheets

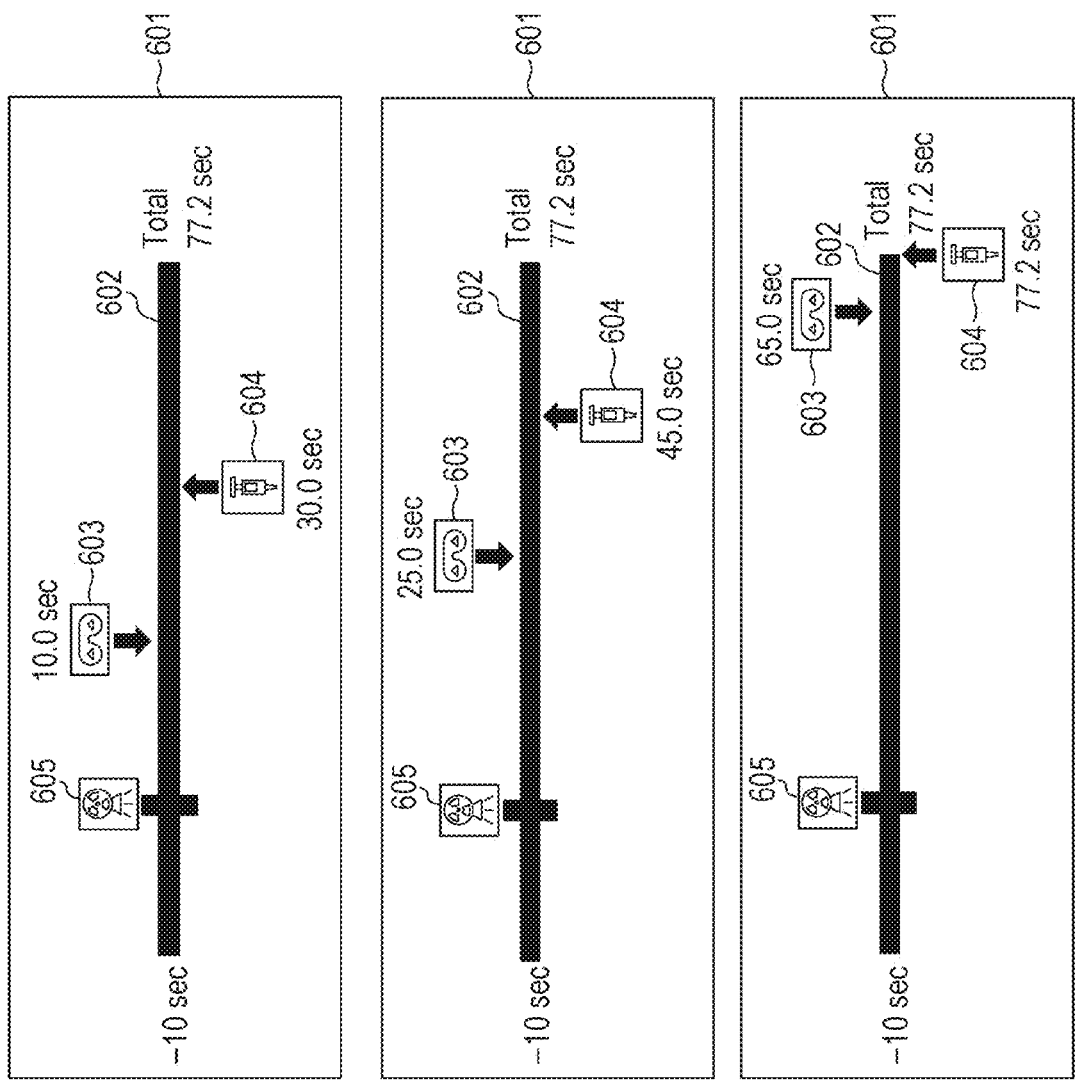

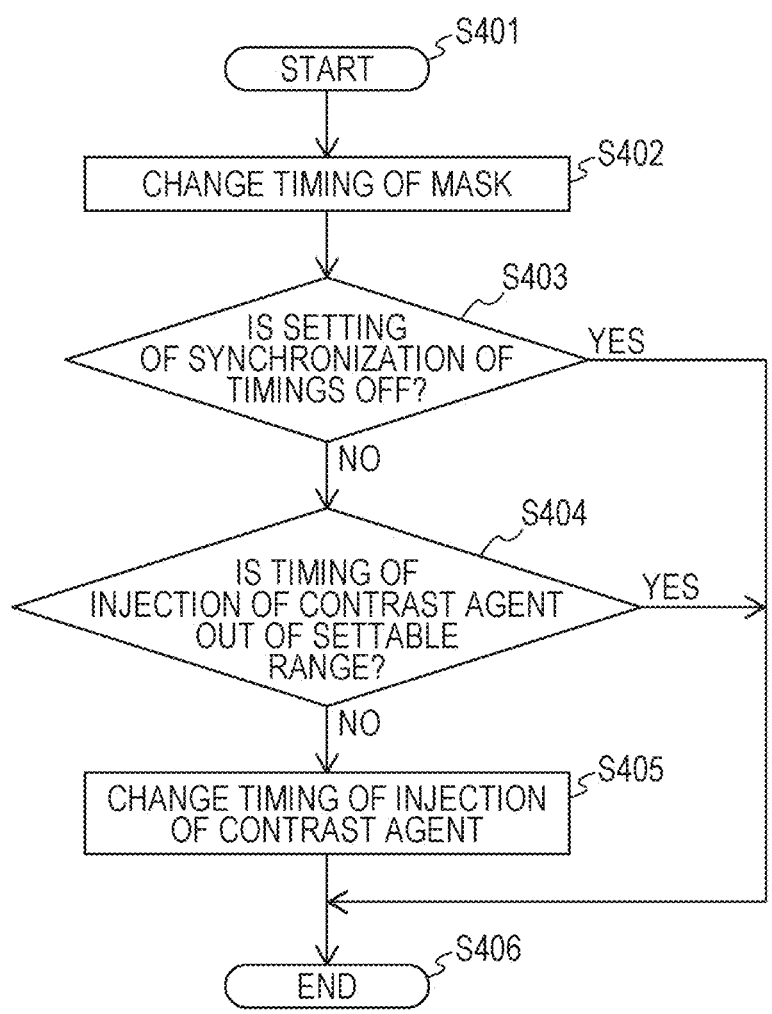

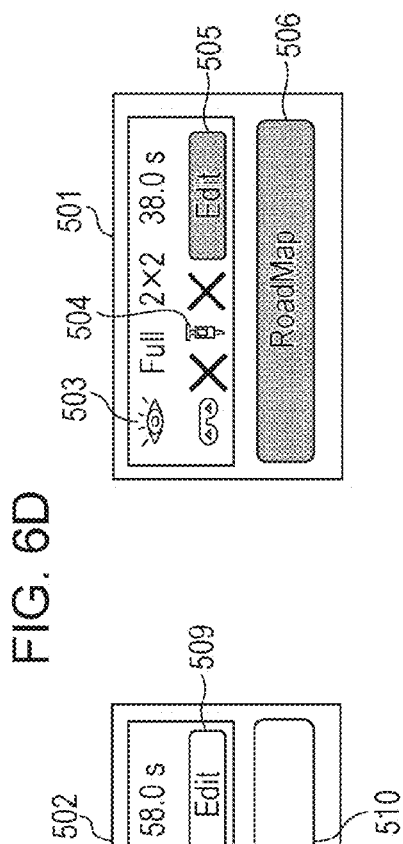
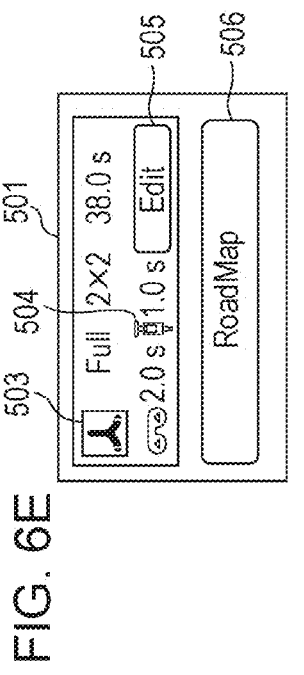
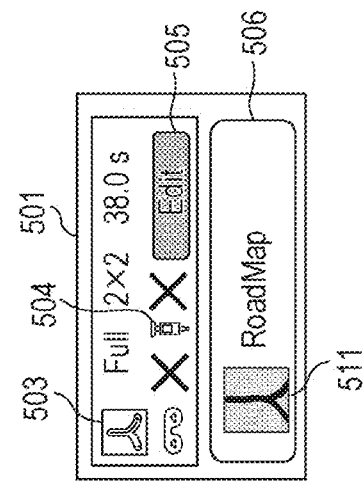
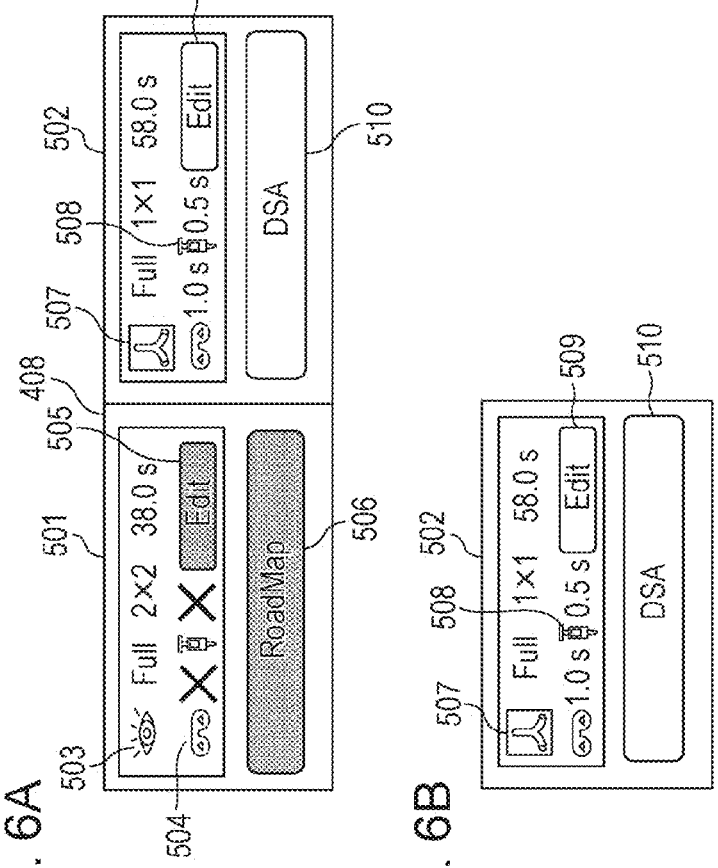
FIG. 6A  FIG. 6B  FIG. 6C  FIG. 6D  FIG. 6E  FIG. 6F

RADIATION IMAGING SYSTEM AND METHOD FOR CONTROLLING THE SAME

BACKGROUND OF THE INVENTION

1. Field of the Invention

The present invention relates to a radiation imaging system which performs a subtraction process using a mask image which is a normal fluoroscopic image and a live image which is a fluoroscopic image which includes an image of a contrast agent.

2. Description of the Related Art

Japanese Patent Laid-Open No. 6-154196 discloses a general radiation imaging system, in particular, a radiation imaging system capable of generating an image by a digital subtraction angiography (DSA) imaging method. Here, a DSA method is an image generation method for performing a subtraction process using a mask image which is a normal fluoroscopic image and a live image which is a fluoroscopic image which includes an image of a contrast agent. In Japanese Patent Laid-Open No. 6-154196, a time chart generated in accordance with a desired calculation is displayed in a display unit so that determination of an imaging procedure is facilitated. Specifically, graphics representing a timing when a mask image is obtained and a timing when a contrast agent is injected which are determined in accordance with a desired calculation are displayed in the display unit relative to a time axis displayed in the display unit. Thereafter, when a marker is moved to one of the graphics in the display unit by operating a pointing device such as a mouse, a numerical value may be input to the graphic by a numerical keypad so that a setting value of a parameter is changed.

SUMMARY OF THE INVENTION

In radiation imaging systems capable of generating an image in a DSA method, sequence control for easily determining timings is demanded. Accordingly, the present invention provides a radiation imaging system which is capable of generating an image by the DSA method and which is further capable of easily performing sequence control.

A radiation imaging system performs a difference process using a mask image which is instructed by a calculation unit to be stored in a storage unit and which is based on a radiation image which is obtained before a contrast agent is injected by an injection device to a certain portion of an object and which is selected from among fluoroscopic images obtained by a radiation imaging apparatus on the basis of a radial ray which is irradiated by a radiation source and which passes the certain portion, and a radiation image which is obtained after the contrast agent is injected and which is selected from among the fluoroscopic images. The radiation imaging system includes a controller configured to display a first graphic representing a first timing when irradiation of a radial ray from the radiation source is started, a second graphic representing a second timing when the mask image is stored, and a third graphic representing a third timing when injection of the contrast agent performed by the injection device is started in a display unit in this order along a time axis displayed in the display unit, control the second timing by a position of the second graphic relative to the time axis, and control the third timing by a position of the third graphic relative to the time axis. When one of the second and third graphics is moved along the time axis, the controller moves the other of the second and third graphics such that an interval between the first and third graphics becomes larger than an interval between the first and second graphics.

A method for controlling a radiation imaging system which performs a difference process using a mask image which is instructed by a calculation unit to be stored in a storage unit and which is based on a radiation image which is obtained before a contrast agent is injected by an injection device to a certain portion of an object and which is selected from among fluoroscopic images obtained by a radiation imaging apparatus on the basis of a radial ray which is irradiated by a radiation source and which passes the certain portion, and a radiation image which is obtained after the contrast agent is injected and which is selected from among the fluoroscopic images. The method includes displaying a first graphic representing a first timing when irradiation of a radial ray from the radiation source is started, a second graphic representing a second timing when the mask image is stored, and a third graphic representing a third timing when injection of the contrast agent performed by the injection device is started in a display unit in this order along a time axis displayed in the display unit, moving, when one of the second and third graphics is moved along the time axis, the other of the second and third graphics such that an interval between the first and third graphics becomes larger than an interval between the first and second graphics, controlling the second timing by a position of the second graphic relative to the time axis, and controlling the third timing by a position of the third graphic relative to the time axis.

Further features of the present invention will become apparent from the following description of exemplary embodiments with reference to the attached drawings.

BRIEF DESCRIPTION OF THE DRAWINGS

FIGS. 2A to 2C are diagrams illustrating examples of screens for explaining display and control of graphics displayed in a display unit according to the first embodiment.

FIG. 3 is a flowchart illustrating the display and the control of the graphics displayed in the display unit according to the first embodiment.

FIGS. 6A to 6F are diagrams illustrating examples of screens displayed in the display unit of the radiation imaging system.

DESCRIPTION OF THE EMBODIMENTS

Hereinafter, embodiments of the present invention will be described in detail with reference to the accompanying drawings. Note that, although cases where an X-ray is used as a radial ray are described as examples in the embodiments below, the radial ray is not limited to an X-ray in this specification and an α-ray, a β-ray, a γ-ray, a particle beam, a cosmic-ray, and the like are also included in the radial ray.

First Embodiment

Figure 1A:
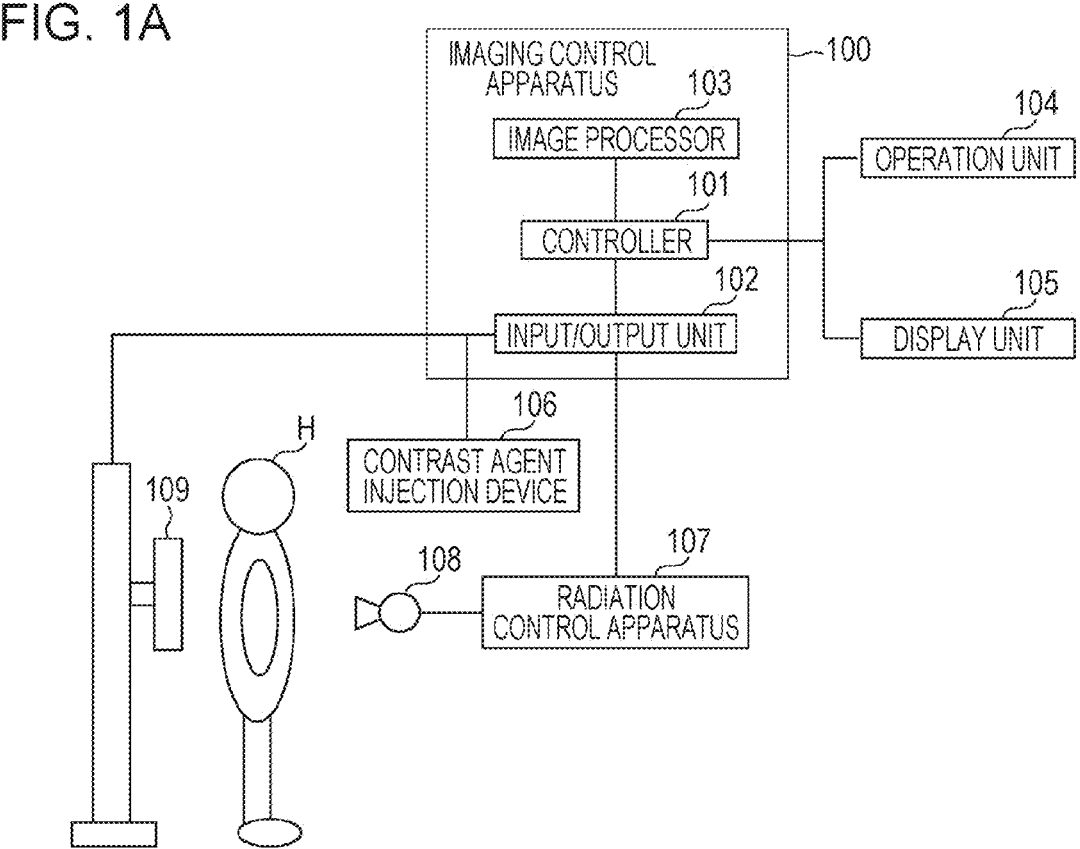
FIG. 1A is a block diagram schematically illustrating an entire radiation imaging system and FIG. 1B is a block diagram schematically illustrating a controller according to a first embodiment.

First, an example of a radiation imaging system will be described with reference to FIG. 1A. FIG. 1A is a block diagram schematically illustrating the entire radiation imaging system. The radiation imaging system includes a radiation imaging apparatus 109, an imaging control apparatus 100, a contrast agent injection device 106, a radiation control apparatus 107, and a radiation source 108. The radiation imaging apparatus 109 obtains a fluoroscopic image based on a radial ray which is irradiated from the radiation source 108 and which passes a certain portion of an object H. As the radiation imaging apparatus 109, a general flat panel detector (FPD) is suitably used. Here, the fluoroscopic image is obtained using a plurality of radiation images consecutively obtained by fluoroscopic imaging using the imaging control apparatus 100. The contrast agent injection device 106 injects a contrast agent to a certain portion (a blood vessel of the examined object, for example) of the object H. The radiation control apparatus 107 controls irradiation of a radial ray performed by the radiation source 108. The imaging control apparatus 100 controls the radiation imaging apparatus 109, the contrast agent injection device 106, and the radiation control apparatus 107 in accordance with instructions input through an operation unit 104 which will be described below. The radiation imaging system may further include the operation unit 104 and a display unit 105. The operation unit 104 may supply operation information used to operate a process performed by the radiation imaging system to the imaging control apparatus 100 in accordance with an input performed by an operator (a photographing operator or a doctor). The display unit 105 serving as an output section which may display an image such as a fluoroscopic image obtained by the imaging control apparatus 100 for the operator is realized as a liquid crystal display, for example. Furthermore, the display unit 105 displays various graphics representing timings in a sequence of operations of the radiation imaging system for the operator. Specifically, the display unit 105 may display graphical user interfaces (GUIs) of control software of radiation imaging. Here, the operation unit 104 may supply the operation information to the imaging control apparatus 100 by performing image operations on the various graphics displayed in the display unit 105 using an input device such as a mouse or a keyboard. The operation unit 104 and the display unit 105 may be integrally realized as a touch panel or the like.

The imaging control apparatus 100 may include an input/output unit 102, an image processor 103, and a controller 101. The input/output unit 102 receives a radiation image input from the radiation imaging apparatus 109 and outputs control signals to the contrast agent injection device 106 and the radiation control apparatus 107. The image processor 103 performs various correction processes including offset correction, gain correction, and defect correction and various image processes including gradation conversion and a dynamic range compression process on a radiation image supplied from the radiation imaging apparatus 109. The controller 101 may output control signals for various control operations to the radiation imaging apparatus 109, the contrast agent injection device 106, and the radiation control apparatus 107 through the input/output unit 102 in accordance with the operation information supplied from the operation unit 104.

Figure 1B:
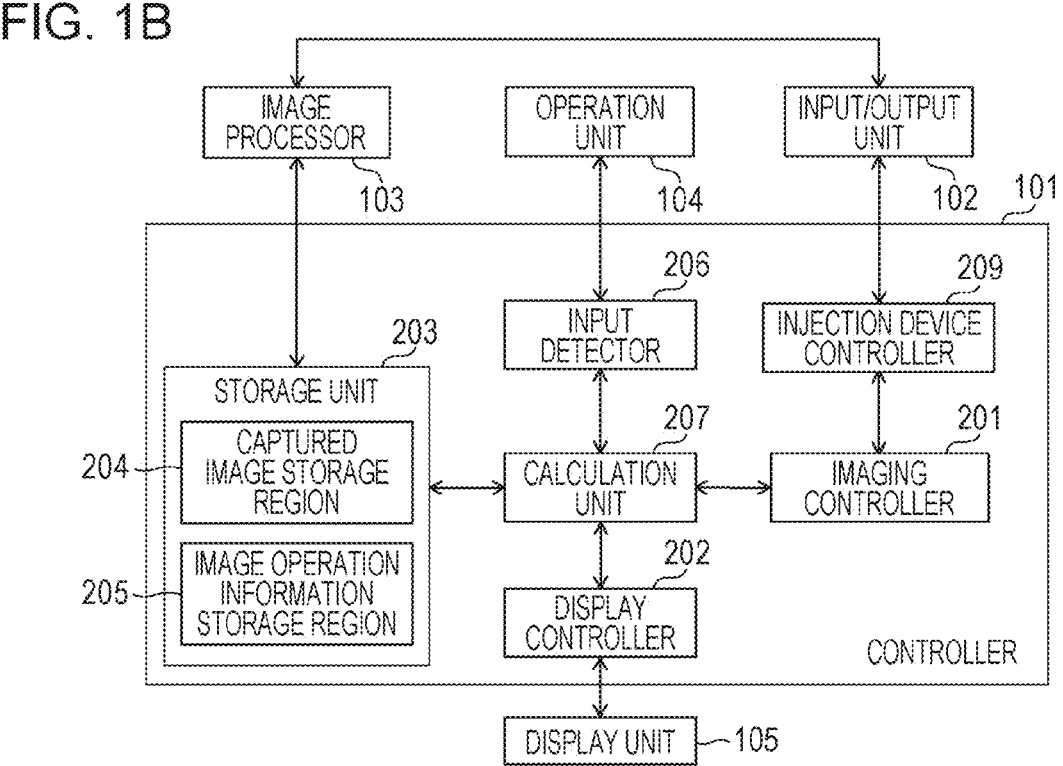

Next, the controller 101 will be described with reference to FIG. 1B. FIG. 1B is a block diagram schematically illustrating functional blocks of the controller 101. The controller 101 may include an input detector 206, a storage unit 203, a calculation unit 207, a display controller 202, an imaging controller 201, and an injection device controller 209. The input detector 206 supplies the operation information input by the operation unit 104 to the calculation unit 207. The storage unit 203 includes a captured image storage region 204 which may store radiation images which have been subjected to image processing performed by the image processor 103. The storage unit 203 further includes an image operation information storage region 205 which may store information on the various graphics serving as the GUIs such as various icons, various operation buttons, and various display regions which are to be displayed in the display unit 105 and information on display positions of the graphics. The calculation unit 207 may instruct the display controller 202 to display the GUIs in the display unit 105 in accordance with various information stored in the image operation information storage region 205.

Furthermore, the calculation unit 207 may perform calculation relating to display control in accordance with the operation information supplied from the input detector 206 and the various information stored in the image operation information storage region 205 and issue an instruction to the display controller 202 for causing the display unit 105 to perform display in accordance with a result of the calculation. The display controller 202 controls the display of the display unit 105 in accordance with the result of the calculation performed by the calculation unit 207. Furthermore, the calculation unit 207 performs calculation relating to imaging control in accordance with the operation information supplied from the input detector 206 and the various information stored in the image operation information storage region 205 and supplies a result of the calculation to the imaging controller 201. The imaging controller 201 controls operation of the radiation imaging apparatus 109 in accordance with a result of the calculation performed by the calculation unit 207. Furthermore, the imaging controller 201 supplies information on control of operation of the contrast agent injection device 106 to the injection device controller 209 in accordance with the result of the calculation performed by the calculation unit 207. The injection device controller 209 controls operation of the contrast agent injection device 106 in accordance with the supplied information.

In the radiation imaging system configured as described above, a mask image is generated in accordance with a radiation image obtained before a contrast agent is injected to a certain portion by the contrast agent injection device 106. The mask image may be selected from among obtained fluoroscopic images and the calculation unit 207 causes the storage unit 203 to store the mask image. Furthermore, in the radiation imaging system, the calculation unit 207 may perform a difference process using the radiation image obtained after the contrast agent is injected and selected from among the fluoroscopic images and the mask image stored in the storage unit 203 so as to generate a difference image. An imaging method (image generation method) of the radiation imaging system capable of generating such a difference image is referred to as a digital subtraction angiography (DSA) method. The controller 101 is capable of selectively performing a plurality of image generation methods.

Sequence control is required for easily determining timings in the radiation imaging system capable of generating images by the DSA method. Accordingly, in the present invention, sequence control described with reference to FIGS. 2A to 2C below is provided.

FIGS. 2A to 2C are diagrams illustrating screens for explaining display and control of the graphics in the display unit 105. Here, the display unit 105 may display a time axis 602, a first graphic 605, a second graphic 603, and a third graphic 604 in a timing setting region 601 in accordance with a display instruction supplied from the controller 101. The first graphic 605 is an icon representing a timing (first timing) when irradiation of a radial ray is started by the radiation source 108. The time axis 602 serves as a slider which specifies a period of time in which irradiation of a radial ray is performed. A period of time before the irradiation of a radial ray is started is displayed on a first end of the time axis 602 and a period of time after the irradiation of a radial ray is started is displayed on a second end so that the period of time in which the irradiation of a radial ray is performed is specified. In FIG. 2A, "−10 seconds" is set in the first end whereas "77.2 seconds" is set in the second end, that is, the period of time in which the irradiation of a radial ray is performed is 67.2 seconds. The second graphic 603 is an icon representing a timing (second timing) when the storage unit 203 stores a mask image in response to an instruction issued by the calculation unit 207. The third graphic 604 is an icon representing a timing (third timing) when injection of a contrast agent is started by the contrast agent injection device 106. The first graphic 605, the second graphic 603, and the third graphic 604 are displayed in this order in the timing setting region 601 along the time axis 602. In FIG. 2A, "10 seconds" corresponding to the second graphic 603 represents an interval between the first graphic 605 and the second graphic 603. Furthermore, "30 seconds" corresponding to the third graphic 604 represents an interval between the first graphic 605 and the third graphic 604. Here, the intervals are represented by periods of time, for example. The second graphic 603 and the third graphic 604 are displayed so as to be moved along the time axis 602 in accordance with an image operation performed on the display unit 105 by the operation unit 104. The calculation unit 207 performs a calculation process such that the second timing when a mask image is stored is changed by a movement of the second graphic 603 and the third timing when a contrast agent is injected is changed by a movement of the third graphic 604 and supplies a result of the calculation to the imaging controller 201.

When the interval between the first graphic 605 and the second graphic 603 becomes larger than the interval between the first graphic 605 and the third graphic 604 due to such a movement operation, the timing when injection of a contrast agent is started comes before the timing when a mask image is stored. Accordingly, a mask image is generated in accordance with a radiation image including an image of the contrast agent, and therefore, an image of a blood vessel to which the contrast agent is injected is not reliably reflected in a difference image to be obtained.

Therefore, as illustrated in FIG. 2B, when one of the second graphic 603 and the third graphic 604 is moved along the time axis 602, the controller 101 moves the other one of the second graphic 603 and the third graphic 604 so that the interval between the first graphic 605 and the third graphic 604 becomes larger than the interval between the first graphic 605 and the second graphic 603. When the second graphic 603 is moved along the time axis 602 by an image operation, for example, the controller 101 moves the third graphic 604 such that the interval between the first graphic 605 and the third graphic 604 becomes larger than the interval between the first graphic 605 and the second graphic 603. Since the order of the first graphic 605, the second graphic 603, and the third graphic 604 is determined in advance, the timing when injection of a contrast agent is started is prevented from coming before the timing when a mask image is stored by performing such control. In FIG. 2B, the second graphic 603 is moved by an image operation so that the interval between the first graphic 605 and the second graphic 603 increases by 15 seconds when compared with FIG. 2A. Accordingly, the controller 101 moves the third graphic 604 so that the interval between the first graphic 605 and the third graphic 604 also increases by 15 seconds.

Meanwhile, the controller 101 moves the third graphic 604 along with the movement of the second graphic 603 so that an interval between the second graphic 603 and the third graphic 604 of 20 seconds is maintained. In this way, in accordance with movement of one of the second graphic 603 and the third graphic 604 along the time axis 602, the controller 101 moves the other one of the second graphic 603 and the third graphic 604 so that the predetermined interval between the second graphic 603 and the third graphic 604 is maintained. By the movement, a time interval, which is appropriately set in advance, between the timing when a mask image is stored and the timing when a contrast agent is injected may be maintained with ease.

Furthermore, as illustrated in FIG. 2C, when the third graphic 604 reaches the second end of the time axis 602, the controller 101 cancels the maintaining of the interval between the second graphic 603 and the third graphic 604. In FIG. 2C, when the second graphic 603 is moved along the time axis 602 by an image operation, the third graphic 604 reaches the second end of the time axis 602 represented by "77.2 seconds". Meanwhile, the second graphic 603 is moved to a position corresponding to "65.0 seconds" by the image operation, and therefore, the interval between the second graphic 603 and the third graphic 604 is reduced to 12.2 seconds, that is, reduced by 2.8 seconds. By this control, flexible sequence control is realized by a simple image operation.

Next, a control operation for setting the second timing when a mask image is stored and the third timing when injection of a contrast agent is started will be described with reference to FIG. 3. FIG. 3 is a flowchart illustrating settings of the second timing when a mask image is stored and the third timing when injection of a contrast agent is started. First, when a sequence is started in a state in which the timing setting region 601 illustrated in FIG. 2A is displayed in the display unit 105 (S401), an operator moves the second graphic 603 along the time axis 602 by an image operation using the operation unit 104 (S402). Here, as illustrated in FIG. 2B, the second graphic 603 is moved from a position corresponding to "10 seconds" illustrated in FIG. 2A to a position corresponding to "25 seconds". Here, the controller 101 determines whether a setting for maintaining the interval between the second graphic 603 and the third graphic 604 is in an on state or an off state. When the setting is in the off state, the controller 101 does not move the third graphic 604 and terminates the process. On the other hand, when the setting is in the on state, the controller 101 determines whether the third graphic 604 has reached the second end of the time axis 602 (that is, whether the third timing when injection of a contrast agent is started is out of a settable range) (S404). When the third graphic 604 has reached the second end as illustrated in FIG. 2C, the controller 101 terminates the movement of the third graphic 604. On the other hand, when the third graphic 604 has not reached the second end as illustrated in FIG. 2B, the controller 101 moves the third graphic 604 along with the movement of the second graphic 603 so that the interval between the first graphic 605 and the third graphic 604 becomes larger than the interval between the first graphic 605 and the second graphic 603. By this, the third timing when injection of a contrast agent is started is changed (S405), the calculation unit 207 controls the storage unit 203 in accordance with the movements of the second graphic 603 and the third graphic 604, and the injection device controller 209 controls the contrast agent injection device 106.

Next, an example of an examining/imaging sequence performed by the radiation imaging system of the present invention will be described with reference to FIG. 4A to FIG. 8.

Figure 4A:
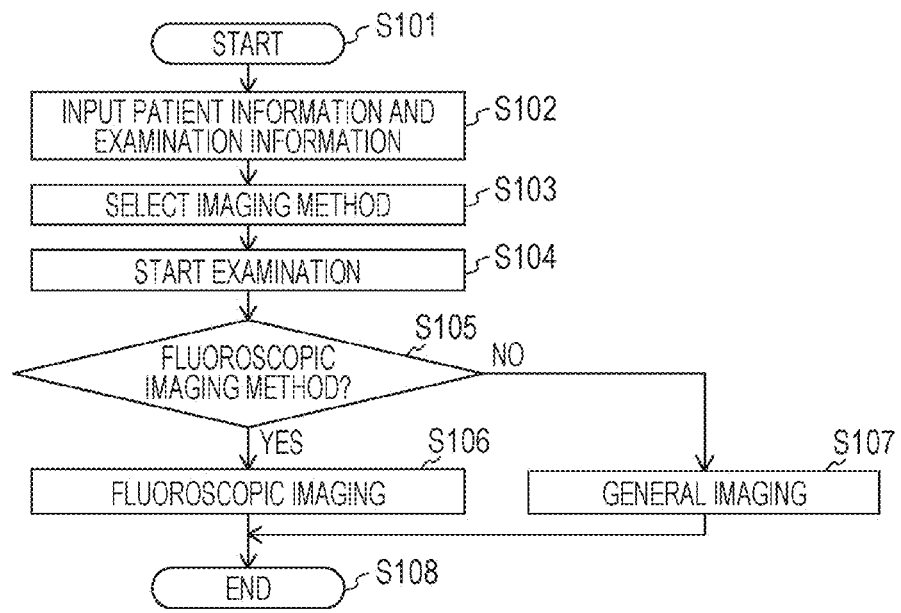
FIG. 4A is a flowchart illustrating an example of a sequence of operations performed by the radiation imaging system and FIGS. 4B and 4C are diagrams illustrating examples of examination information input screens.
Figure 4B:
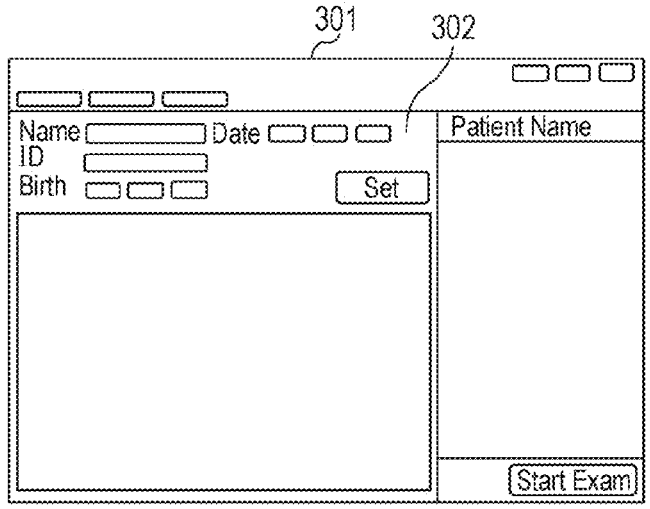
Figure 4C:
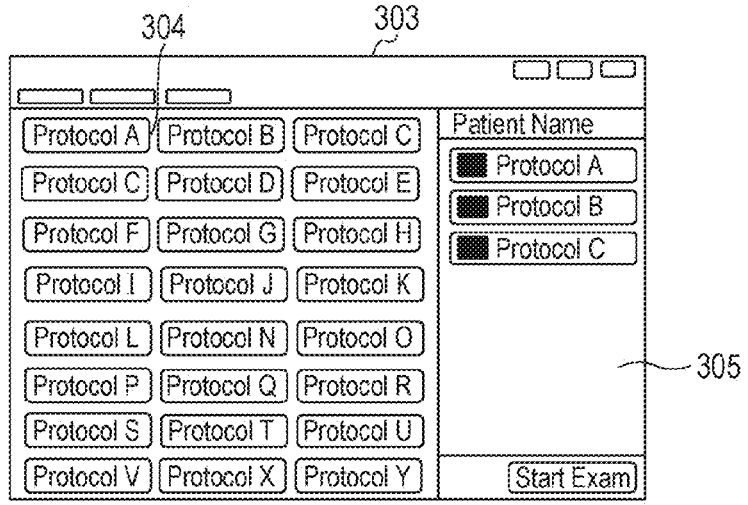

First, an entire examining/imaging sequence and display screens of the display unit 105 used for image operations will be described with reference to FIGS. 4A to 4C. FIG. 4A is a flowchart illustrating the entire examining/imaging sequence, and FIGS. 4B and 4C are display screens of the display unit 105 used for image operations. First, the radiation imaging system is activated (S101) and an examination information input screen 301 is displayed in the display unit 105 as illustrated in FIG. 4B. Subsequently, the operator inputs, using the operation unit 104, information on a patient to be examined and examination information in an examination information input region 302 of the examination information input screen 301 (S102). Thereafter, the operator selects an imaging method to be used in the examination from among a plurality of imaging methods displayed as buttons in an imaging method selection region 304 in an imaging method selection screen 303 illustrated in FIG. 4C by an image operation using the operation unit 104 (S103). The selected imaging method is displayed in an imaging information display region 305 in the imaging method selection screen 303 and the examination is started (S104). When the examination is started, the controller 101 determines whether the selected imaging method corresponds to a general imaging mode or a fluoroscopic imaging mode (S105). When it is determined that the selected imaging method corresponds to the fluoroscopic imaging mode, the controller 101 instructs the radiation imaging apparatus 109 to perform fluoroscopic imaging and executes the selected imaging method (S106). On the other hand, when it is determined that the selected imaging method corresponds to the general imaging mode, the controller 101 instructs the radiation imaging apparatus 109 to perform general imaging and executes the selected imaging method (S107). After the execution of the selected imaging method is terminated, the examining/imaging sequence is terminated (S108).

Figure 5A:
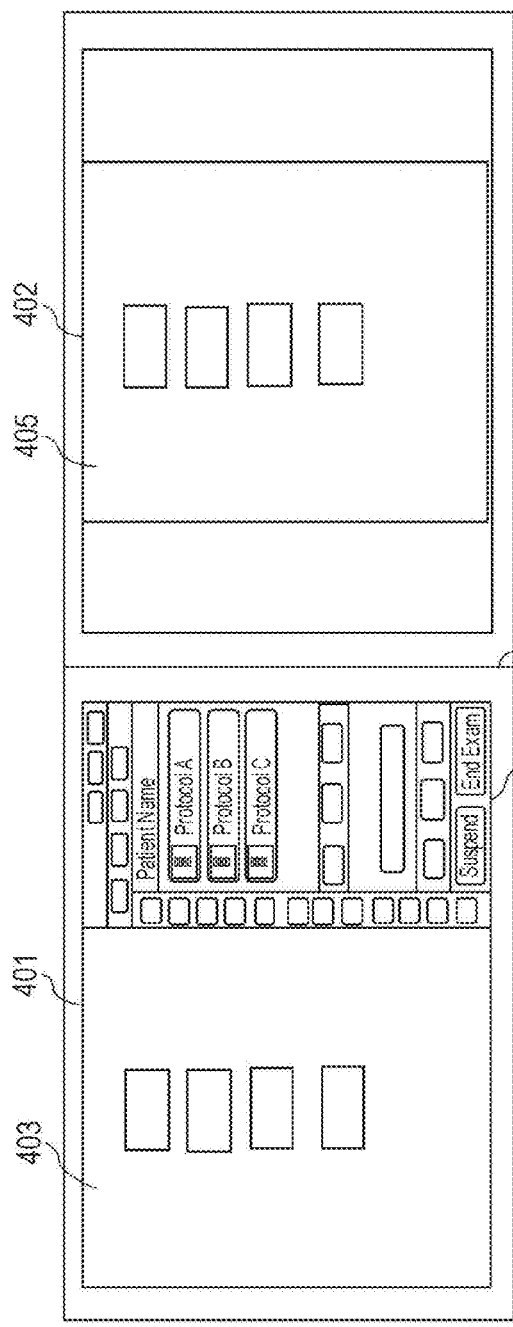
FIGS. 5A and 5B are diagrams illustrating examples of screens displayed in the display unit of the radiation imaging system.
Figure 5B:
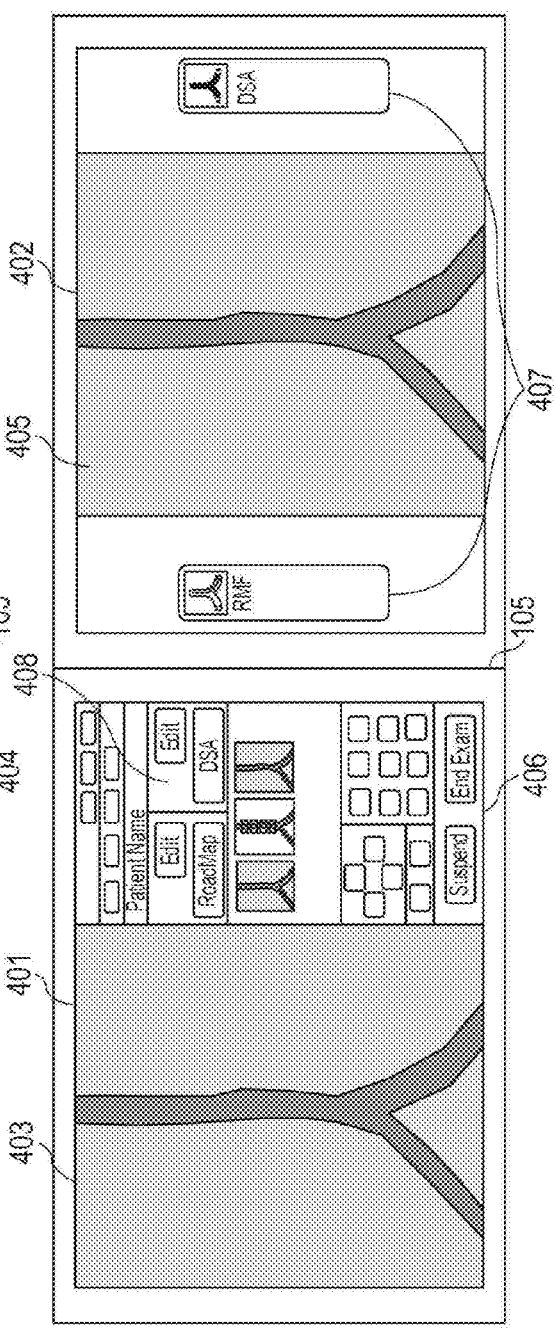
Figure 7:
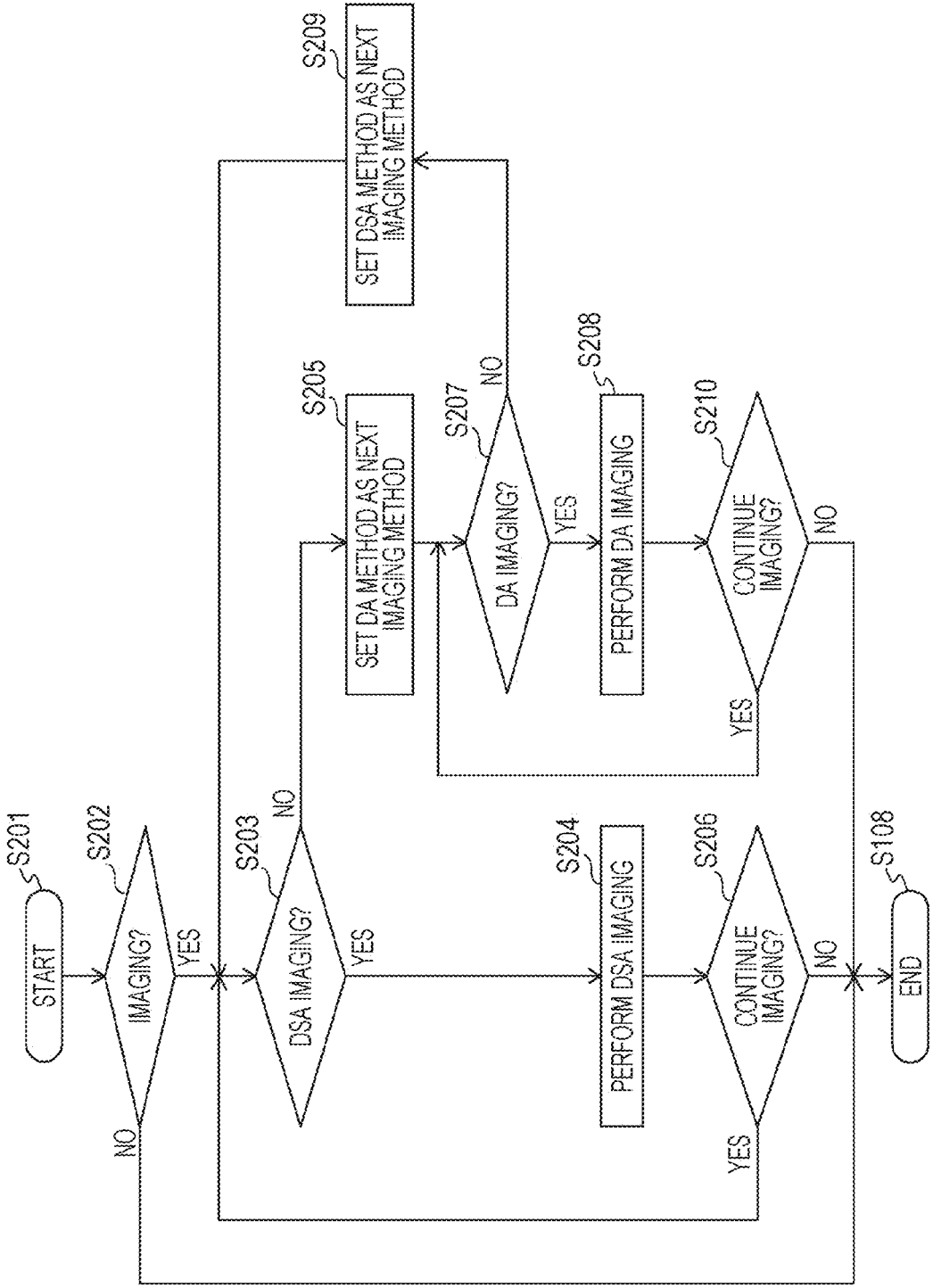
FIG. 7 is a flowchart illustrating an example of a sequence of operations of the radiation imaging system.
Figure 8:
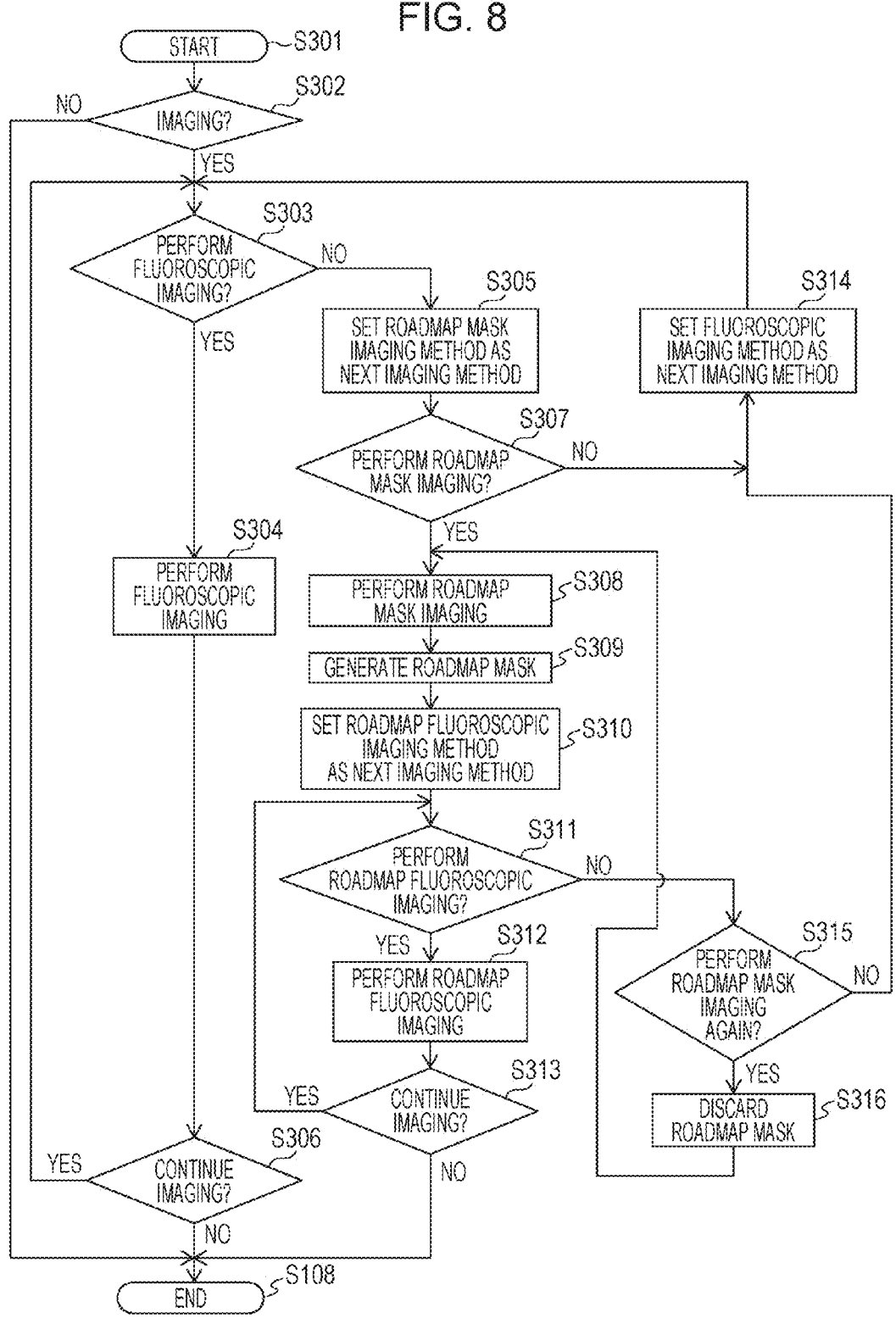
FIG. 8 is a flowchart illustrating an example of another sequence of operations of the radiation imaging system.

Next, a display screen of the display unit 105 obtained when the general imaging mode is selected will be described with reference to FIG. 5A. When the operator performs an image operation on the display screen illustrated in FIG. 5A using the operation unit 104, an imaging sequence of the selected general imaging mode may be executed. In the general imaging mode, first and second screen regions 401 and 402 may be displayed in the display unit 105. The first screen region 401 includes a reference image display region 403 and an image operation region 404 for the general imaging mode. The reference image display region 403 is used to display images which have been captured in the past. When the images included in the reference image display region 403 are to be switched from one to another, an image operation of selecting a desired imaging method from among the plurality of imaging methods represented as the buttons in the image operation region 404 for the general imaging mode is performed. The second screen region 402 includes a latest image display region 405. The latest image display region 405 displays radiation images which are most lately obtained. In FIGS. 5A and 5B, a display employing a two-screen display method is used as the display unit 105.

Next, a display screen of the display unit 105 displayed when the fluoroscopic imaging mode is selected will be described with reference to FIG. 5B. When the operator performs an image operation on the display screen illustrated in FIG. 5B using the operation unit 104, an imaging sequence of the selected fluoroscopic imaging mode may be executed. Components the same as those of the display screen for the general imaging mode illustrated in FIG. 5A are denoted by reference numerals the same as those of the display screen for the general imaging mode and detailed descriptions thereof are omitted. A first screen region 401 for the fluoroscopic imaging mode illustrated in FIG. 5B includes an image operation region 406 for the fluoroscopic imaging mode instead of the image operation region 404 for the general imaging mode illustrated in FIG. 5A, and the image operation region 406 for the fluoroscopic imaging mode includes an imaging setting region 408. The imaging setting region 408 will be described in detail with reference to FIG. 6. The imaging setting region 408 is used when an image operation of setting an imaging sequence to be performed next is performed. A second screen region 402 for the fluoroscopic imaging mode illustrated in FIG. 5B additionally includes latest-imaging information regions 407. The latest-imaging information regions 407 may display information on imaging methods used to obtain an image displayed in a latest image display region 405.

Note that, in this radiation imaging system, five imaging methods, that is, the DSA imaging method, a digital angiography (DA) imaging method, a roadmap mask imaging method, a roadmap fluoroscopic method, and a fluoroscopic method, may be executed. In the DSA imaging method, a difference process is performed using a radiation image which is obtained after a contrast agent is injected and which is selected from among fluoroscopic images and a mask image stored in the storage unit 203 so as to generate a difference image. In the DA imaging method, a fluoroscopic image is stored. Preferably, in the DA imaging method, a fluoroscopic image including a radiation image obtained after a contrast agent is injected among fluoroscopic images is generated. In the roadmap mask imaging method, an image of a blood vessel to which a contrast agent is injected is generated by performing a maximum intensity projection process (MIP process) on an image obtained by performing a difference process using a radiation image which is obtained after a contrast agent is injected and which is selected from among fluoroscopic images and a mask image. The image of the blood vessel to which the contrast agent is injected corresponds to a roadmap mask image used in the roadmap fluoroscopic imaging method described below, and an imaging method for generating a roadmap mask image is referred to as the "roadmap mask imaging method". In the roadmap fluoroscopic imaging method, a difference process is performed using a fluoroscopic image obtained by the radiation imaging apparatus and a roadmap mask image so that a fluoroscopic image in which the image of the blood vessel is reflected is obtained. The roadmap fluoroscopic imaging method may correspond to an image generation method for generating an image of a blood vessel of a certain portion to which a catheter is inserted, for example. In the fluoroscopic imaging method, a fluoroscopic image is obtained in a state in which a contrast agent has not been injected. Among the five imaging methods, the DSA method includes the DSA imaging method and the roadmap mask imaging method, and the DSA imaging method corresponds to a first method of the present invention and the roadmap mask imaging method corresponds to a second method of the present invention.

Next, various image operation regions displayed in the imaging setting region 408 will be described with reference to FIGS. 6A to 6F. The imaging setting region 408 includes a first imaging method group setting region 502 and a second imaging method group setting region 501. In the first imaging method group setting region 502, an image operation of setting an imaging condition in the DSA imaging method or the DA imaging method is performed. In the second imaging method group setting region 501, an image operation of setting an imaging condition in the roadmap mask imaging method, the roadmap fluoroscopic imaging method, or the fluoroscopic imaging method is performed.

The first imaging method group setting region 502 includes a first imaging information display region 507, a first imaging timing display region 508, a timing edit region 509, and an imaging method switching region 510. The first imaging information display region 507 is used to display an icon representing a selected imaging method. In FIGS. 6A and 6B, an icon representing the DSA imaging method is displayed, and in FIG. 6C, an icon representing the DA imaging method is displayed. The first imaging timing display region 508 is used to display the timing when a mask image is obtained and the timing when injection of a contrast agent is started. In examples illustrated in FIGS. 6A to 6C, the timings may be displayed when the imaging methods included in the DSA method are employed whereas "x" may be displayed when the imaging method which is not included in the DSA method is employed. Here, as the timing when injection of a contrast agent is started, a time difference between the timing when a mask image is obtained and the timing when injection of a contrast agent is started is displayed. The timing edit region 509 is used to perform an image operation of screen transition to the timing setting region 601 illustrated in FIGS. 2A to 2C to edit the timing when a mask image is obtained and the timing when injection of a contrast agent is started. In the examples illustrated in FIGS. 6A to 6C, the timing edit region 509 is represented as a button, and the screen transition to the timing setting region 601 is executed by selecting the button by an image operation. Furthermore, in the DA imaging method illustrated in FIG. 6C, since the timings are not required to be selected, the timing edit region 509 is displayed not to be selected and image operation is invalid. The imaging method switching region 510 is used to perform an image operation of performing switching between the DSA imaging method and the DA imaging method. In the examples illustrated in FIGS. 6A to 6C, the imaging method switching region 510 is displayed as a button. When the button is selected in a state in which selection of the DSA imaging method illustrated in FIGS. 6A and 6B is displayed, display representing that the DA method is selected is performed in a switching manner as illustrated in FIG. 6C.

The second imaging method group setting region 501 includes a second imaging information display region 503, a second imaging timing display region 504, a timing edit region 505, and an imaging method switching region 506. The second imaging information display region 503 is used to display an icon representing a selected imaging method. An icon representing the fluoroscopic imaging method is displayed in FIG. 6D, an icon representing the roadmap mask imaging method is displayed in FIG. 6E, and an icon representing the roadmap fluoroscopic imaging method is displayed in FIG. 6F. The second imaging timing display region 504 is used to display the timing when a mask image is obtained and the timing when injection of a contrast agent is started. In examples illustrated in FIGS. 6D to 6F, the timings may be displayed when the imaging method included in the DSA method is employed whereas "x" may be displayed in the imaging methods which are not included in the DSA method. Here, as the timing when injection of a contrast agent is started, a time difference between the timing when a mask image is obtained and the timing when injection of a contrast agent is started is displayed. The timing edit region 505 is used to perform an image operation of performing screen transition to the timing setting region 601 illustrated in FIGS. 2A to 2C to edit the timing when a mask image is obtained and the timing when injection of a contrast agent is started. In the examples illustrated in FIGS. 6D to 6F, the timing edit region 505 is represented as a button, and the screen transition to the timing setting region 601 is performed by selecting the button by an image operation. Furthermore, in the imaging methods illustrated in FIGS. 6D and 6F which are not included in the DSA method, since the timings are not required to be selected, the timing edit region 505 is displayed not to be selected and an image operation is invalid. The imaging method switching region 506 is used to perform an image operation of performing switching among the three imaging methods. In examples illustrated in FIGS. 6D to 6F, the imaging method switching region 506 is displayed as a button. In FIG. 6D, the fluoroscopic imaging method is selected. Furthermore, the roadmap mask imaging method is selected in FIG. 6E, and the roadmap fluoroscopic imaging method is selected in FIG. 6F. When the roadmap fluoroscopic imaging method is selected as illustrated in FIG. 6F, a thumbnail 511 of a roadmap mask image used in the roadmap fluoroscopic imaging method is displayed in the imaging method switching region 506. When the imaging method switching region 506 of a button shape is selected by an image operation, one of the various methods may be appropriately selected.

Next, a sequence for setting an imaging condition of the DSA imaging method or the DA imaging method will be described with reference to FIGS. 6A to 6C and FIG. 7. First, when a button representing the DSA imaging method or the DA imaging method is selected in the imaging method selection screen 303 illustrated in FIG. 4C in step S103 of FIG. 4A, display for the fluoroscopic imaging mode illustrated in FIG. 5B is performed on the display unit 105 and a setting of an imaging condition is started (S201). Note that, as illustrated in FIG. 6A, the DSA imaging method is selected in this embodiment. Next, the controller 101 determines whether imaging is to be performed in accordance with an image operation performed by the operator using the operation unit 104 (S202). Specifically, the controller 101 determines whether imaging is to be performed in accordance with a determination as to whether a button of "End Exam" included in the image operation region 406 in the fluoroscopic imaging mode illustrated in FIG. 5B is selected. When the button of "End Exam" is selected (No), the controller 101 determines that the imaging is not to be performed and terminates the imaging (S108). On the other hand, when the button of "End Exam" is not selected (Yes), the controller 101 determines that the imaging is to be performed and proceeds to a step of determining an imaging method (S203). In step S203, when the state of FIGS. 6A and 6B is detected, it is determined that the DSA imaging method has been selected (Yes). In this case, the DSA imaging is performed in accordance with set timings in response to an instruction for irradiating a radial ray issued by the operator (S204). When the timing edit region 509 is selected by an image operation in step S204, the timing setting region 601 illustrated in FIGS. 2A to 2C is displayed in a screen which allows settings of the timings. After the desired imaging, the controller 101 determines whether the imaging is to be continued (S206). When the button of "End Exam" is selected in the image operation region 406 (No), the controller 101 determines that the imaging is not to be continued and terminates the imaging (S108). When any one of the buttons of the imaging methods is selected (Yes), the process returns to step S203. Furthermore, when the state of FIG. 6C is detected in step S203, it is determined that the DA imaging method is selected (No) and the DA imaging method is set as a next imaging method (S205). In step S207, it is determined again whether the DA imaging method is to be performed. When the state of FIG. 6C is not changed (Yes), the DA imaging method is executed in response to an instruction for irradiating a radial ray issued by the operator (S208) whereas when the state is changed to the state of FIG. 6B (No), the imaging method is changed to the DSA imaging method (S209) and the process returns to step S203. After the desired imaging, the controller 101 determines whether the imaging is to be continued (S210). When the button of "End Exam" is selected in the image operation region 406 (No), the controller 101 determines that the imaging is not to be continued and terminates the imaging (S108). When any one of the buttons of the imaging methods is selected (Yes), the process returns to step S207.

Next, a sequence for setting an imaging condition of one of the roadmap mask imaging method, the roadmap fluoroscopic imaging method, and the fluoroscopic imaging method will be described with reference to FIGS. 6D to 6F and FIG. 8. First, in step S103 of FIG. 4A, one of the buttons representing the roadmap mask imaging method, the roadmap fluoroscopic imaging method, and the fluoroscopic imaging method is selected in the imaging method selection screen 303 illustrated in FIG. 4C. Then display corresponding to the fluoroscopic imaging mode is performed on the display unit 105 as illustrated in FIG. 5B, and a setting of an imaging condition is started (S301). As illustrated in FIG. 6D, the fluoroscopic imaging method is selected in this embodiment. Next, the controller 101 determines whether imaging is to be performed in accordance with an image operation performed by the operator using the operation unit 104 (S302). Specifically, the controller 101 determines whether imaging is to be performed in accordance with a determination as to whether the button of "End Exam" included in the image operation region 406 in the fluoroscopic imaging mode illustrated in FIG. 5B is selected. When the button of "End Exam" is selected (No), the controller 101 determines that the imaging is not to be performed and terminates the imaging (S108). On the other hand, when the button of "End Exam" is not selected (Yes), the controller 101 determines that the imaging is to be performed and proceeds to a step of determining an imaging method (S303). In step S303, when the state of FIG. 6D is detected, it is determined that the fluoroscopic imaging method is selected (Yes). In this case, the fluoroscopic imaging is performed in response to an instruction for irradiating a radial ray issued by the operator (S304). After the desired imaging, the controller 101 determines whether the imaging is to be continued (S306). When the button of "End Exam" is selected in the image operation region 406 (No), the controller 101 determines that the imaging is not to be continued and terminates the imaging (S108). When any one of the buttons of the imaging methods is selected (Yes), the process returns to step S303. Furthermore, when the state of FIG. 6E is detected in step S303, it is determined that the roadmap mask imaging method is selected (No) and the roadmap mask imaging method is set as a next imaging method (S305). A determination is performed again so as to determine whether the roadmap mask imaging method is to be executed in step S307. When the state of FIG. 6E is not changed (Yes), the roadmap mask imaging method is executed in response to an instruction for irradiating a radial ray issued by the operator (S308) so that a roadmap mask image is generated (S309). When the timing edit region 509 is selected by an image operation in step S307, the timing setting region 601 illustrated in FIGS. 2A to 2C is displayed in a screen which allows settings of the timings. When the state of FIG. 6D is detected in step S307 (No), the fluoroscopic imaging method is selected (S314), and the process returns to step S303. When the roadmap mask image is obtained in step S309, the controller 101 changes the display screen of the display unit 105 from the state in FIG. 6E to the state in FIG. 6F so as to select the roadmap fluoroscopic imaging method as a next imaging method (S310). Subsequently, the operator determines whether the roadmap fluoroscopic imaging method is to be executed (S311). When the operator determines that the roadmap fluoroscopic imaging method is to be executed (Yes), the controller 101 performs the roadmap fluoroscopic imaging in response to an instruction for irradiating a radial ray issued by the operator (S312). On the other hand, when the operator determines that the roadmap fluoroscopic imaging method is not to be executed (No), the controller 101 determines whether the roadmap mask imaging is to be performed again by an image operation performed by the operator (S315). For example, when the thumbnail 511 of the roadmap mask image is selected by an image operation performed by the operator, the controller 101 determines to perform the roadmap mask imaging again (Yes). By this, the calculation unit 207 of the controller 101 instructs the storage unit 203 to discard the roadmap mask image (S316) and the process returns to step S308. Note that the controller 101 may determine whether the roadmap mask imaging is to be performed again (Yes) by causing the operator to select a dedicated image region provided in FIG. 6F for the instruction for discarding the roadmap mask image by an image operation. On the other hand, when the imaging method switching region 506 is selected by an image operation in step S315, the controller 101 changes the screen illustrated in FIG. 6F to the screen illustrated in FIG. 6D, and returns to step S314. After the roadmap fluoroscopic imaging is performed (S312), the controller 101 determines whether the imaging is to be continuously performed (S313). When the button of "End Exam" is selected in the image operation region 406 (No), the controller 101 determines that the imaging is not to be continuously performed and terminates the imaging (S108). When any one of the buttons of the imaging methods is selected (Yes), the process returns to step S311.

Second Embodiment

Next, a controller 101 according to a second embodiment will be described with reference to FIG. 9. Components the same as those of the controller 101 of the first embodiment illustrated in FIG. 1B are denoted by reference numerals the same as those of the controller 101 of the first embodiment, and detailed descriptions thereof are omitted. Hereinafter, portions different from the first embodiment illustrated in FIG. 1B will be described with reference to FIG. 9.

Figure 9:
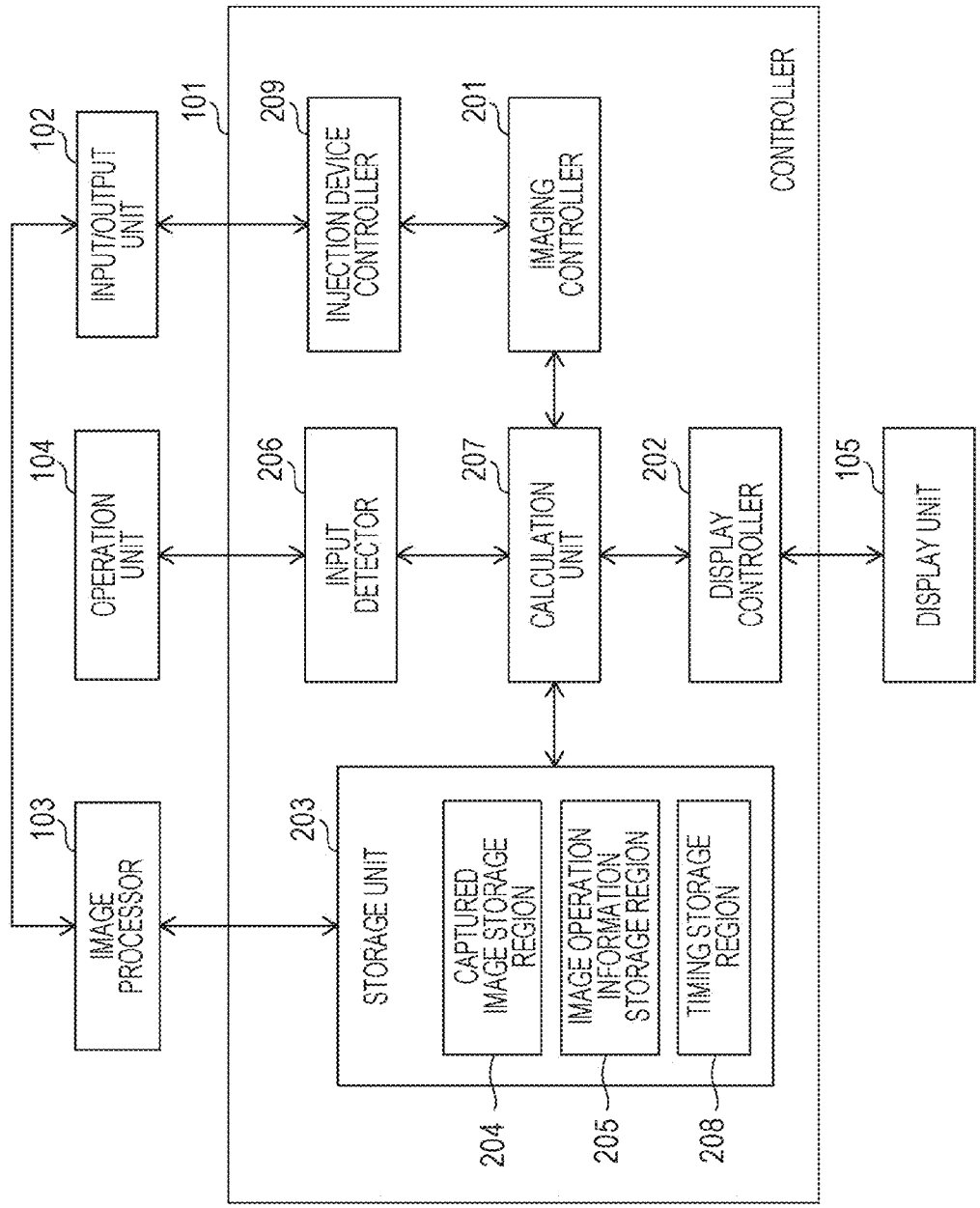
FIG. 9 is a block diagram schematically illustrating a controller according to a second embodiment.

The second embodiment illustrated in FIG. 9 is different from the first embodiment illustrated in FIG. 1B in that a storage unit 203 additionally includes a timing storage region 208. The timing storage region 208 stores a plurality of second timings when a mask image is stored and a plurality of third timings when injection of a contrast agent is started corresponding to various imaging methods included in a DSA method. When at least one of the second and third timings of one of the imaging methods is changed, a calculation unit 207 reflects the change in the other imaging methods, that is, one of the second and third timings of each of the other imaging methods is changed. In this way, since the calculation unit 207 controls the storage unit 203 such that information on the second and third timings is corrected in association with one of the other image generation methods, simple sequence control is realized.

Note that an appropriate combination of the foregoing embodiments is included in the embodiments of the present invention. Furthermore, a case where the foregoing processes are realized by programs and hardware which operate in combination is also included in the embodiments of the present invention. In an embodiment of the programs, the programs corresponding to the foregoing processes and other programs are stored in the storage unit 203, a CPU included in the controller 101 develops the programs in a RAM, and the CPU executes instructions included in the programs.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-127974, filed Jun. 18, 2013, which is hereby incorporated by reference herein in its entirety.

What is claimed is:

1. An X-ray imaging system which performs a difference process using a mask image which is instructed by a calculation unit to be stored in a storage unit and which is based on an X-ray image which is obtained before a contrast agent is injected by an injection device to a certain portion of an object and which is selected from among fluoroscopic images obtained by an X-ray imaging apparatus on the basis of an X-ray which is irradiated by an X-ray source and which passes the certain portion, and an X-ray image which is obtained after the contrast agent is injected and which is selected from among the fluoroscopic images, the X-ray imaging system comprising:
a controller configured to display a first graphic representing a first timing when irradiation of an X-ray from the X-ray source is started, a second graphic representing a second timing when the mask image is stored, and a third graphic representing a third timing when injection of the contrast agent performed by the injection device is started in a display unit in this order along a time axis displayed in the display unit, configured to control the second timing by a position of the second graphic relative to the time axis, and configured to control the third timing by a position of the third graphic relative to the time axis,
wherein, when one of the second and third graphics is moved along the time axis, the controller moves the other of the second and third graphics such that an interval between the first and third graphics becomes larger than an interval between the first and second graphics.

2. The X-ray imaging system according to claim 1, wherein the controller moves one of the second and third graphics in accordance with movement of the other of the second and third graphics relative to the time axis such that a predetermined interval between the second and third graphics is maintained.

3. The X-ray imaging system according to claim 2, wherein when the third graphic reaches an end of the time axis, the controller cancels the maintaining of the interval.

4. The X-ray imaging system according to claim 1, wherein the controller is capable of selectively performing a plurality of image generation methods in the X-ray imaging system, and specifies, in accordance with movement of the second and third graphics in a certain image generation method selected from among the image generation methods, positions of the second and third graphics relative to the time axis in one of the other image generation methods.

5. The X-ray imaging system according to claim 4, wherein the storage unit is capable of storing a plurality of information items relating to the second timing and a plurality of information items relating to the third timing which correspond to the image generation methods, and the controller corrects information on the second timing and information on the third timing which correspond to the certain image generation method selected from among the plurality of image generation methods in accordance with movement of the second and third graphics in the certain image generation method, and corrects information on the second timings and information on the third timings which correspond to the other image generation methods.

6. The X-ray imaging system according to claim 4, wherein the plurality of image generation methods include a first method for generating an image of a blood vessel to which the contrast agent is injected by performing a difference process using, among the fluoroscopic images, the X-ray image obtained after the injection of the contrast agent is performed and the mask image and a second method for generating an image of a blood vessel to which the contrast agent is injected by performing a maximum intensity projection process on an image obtained by the difference process using, among the fluoroscopic images, the X-ray image obtained after the injection of the contrast agent is performed and the mask image.

7. The X-ray imaging system according to claim 6, wherein the plurality of image generation methods further include a third method for generating an image obtained by performing a difference process using a fluoroscopic image obtained by the X-ray imaging apparatus on the basis of a radial ray which passes the certain portion into which a catheter is inserted and the image of a blood vessel generated by the second method.

8. The X-ray imaging system according to claim 1, wherein the controller includes a display controller which controls the calculation unit, the storage unit, and the display unit and an injection device controller which controls the injection device.

9. The X-ray imaging system according to claim 1, further comprising:
an operation unit configured to perform an operation of a process of the X-ray imaging system,
wherein the operation unit performs the operation of the process by operating one of the second and third graphics displayed in the display unit, and
the controller controls a timing when the mask image is stored and a timing when injection of the contrast agent is started in accordance with the operation performed by the operation unit.

10. A method for controlling an X-ray imaging system which performs a difference process using a mask image which is instructed by a calculation unit to be stored in a storage unit and which is based on an X-ray image which is obtained before a contrast agent is injected by an injection device to a certain portion of an object and which is selected from among fluoroscopic images obtained by an X-ray imaging apparatus on the basis of an X-ray which is irradiated by an X-ray source and which passes the certain portion, and an X-ray image which is obtained after the contrast agent is injected and which is selected from among the fluoroscopic images, the method comprising:
displaying a first graphic representing a first timing when irradiation of an X-ray from the X-ray source is started, a second graphic representing a second timing when the mask image is stored, and a third graphic representing a third timing when injection of the contrast agent performed by the injection device is started in a display unit in this order along a time axis displayed in the display unit;
moving, when one of the second and third graphics is moved along the time axis, the other of the second and third graphics such that an interval between the first and third graphics becomes larger than an interval between the first and second graphics;
controlling the second timing by a position of the second graphic relative to the time axis; and
controlling the third timing by a position of the third graphic relative to the time axis.

\* \* \* \* \*